US00PP23709P2

(12) United States Plant Patent
Bergeron

(10) Patent No.: US PP23,709 P2
(45) Date of Patent: Jul. 2, 2013

(54) ***HOSTA* PLANT NAMED 'POCKETFUL OF SUNSHINE'**

(50) Latin Name: ***Hosta hybrid* (Tratt.)**
Varietal Denomination: Pocketful of Sunshine

(75) Inventor: Amy Bergeron, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 76 days.

(21) Appl. No.: 13/200,452

(22) Filed: Sep. 23, 2011

Related U.S. Application Data

(60) Provisional application No. 61/459,727, filed on Dec. 17, 2010.

(51) Int. Cl.
*A01H 5/00* (2006.01)

(52) U.S. Cl.
USPC ..... Plt./353

(58) Field of Classification Search
USPC ..... Plt./353
See application file for complete search history.

*Primary Examiner* — June Hwu

(57) ABSTRACT

*Hosta* plant named 'Pocketful of Sunshine' is a new cultivar with rounded, thick, coriaceous leaves having yellow centers and very broad dark green margins and that become cupped in maturity. The habit is compact and dense with rapid growth rate and light lavender flowers are held attractively above foliage suitable as a potted plant, for the garden, and for cut flower or leaf arrangements.

1 Drawing Sheet

Botanical classification: *Hosta* hybrid (Tratt.).
Variety denomination: 'Pocketful of Sunshine'.

BACKGROUND OF THE INVENTION

The present invention relates to the new and distinct cultivar of *hosta* plant, *Hosta* 'Pocketful of Sunshine' was discovered by Amy Bergeron of Holland, Mich. in the fall of 2008 in a batch of *Hosta* 'Rainforest Sunrise' (not patented) at a nursery in Zeeland, Mich. The new plant was an uninduced whole plant mutation. The new plant has been successfully asexually propagated by division and tissue culture at the same nursery in Zeeland, Mich. since August 2009 and found to be stable and produce identical plants that maintain the unique characteristics of the original plant in successive generations of asexual propagation.

BRIEF SUMMARY OF THE INVENTION

*Hosta* 'Pocketful of Sunshine' differs from its parent, 'Rainforest Sunshine', as well as all other *hostas* known to the applicant. The most similar *hosta* cultivars known to the inventor are: 'Little Sunspot' (not patented), 'Rainforest Sunrise' (not patented), and 'Just So' (not patented). The new plant and the three most similar all have yellow foliage with green margins. *Hosta* 'Rainforest Sunrise' is a green-margined sport from *Hosta* 'Maui Buttercups' (not patented). *Hosta* 'Little Sunspot' and 'Just So' are both sports of *Hosta* 'Little Aurora' (not patented). 'Rainforest Sunrise' and the new plant, 'Pocketful of Sunshine' are both nearly twice the size of 'Little Sunspot and 'Just So' in both plant habit and leaf blade. The new plant and 'Little Sunspot' both have wider margins than their sport parents 'Rainforest Sunrise' and 'Little Aurora' respectively. In comparison, the new plant has variegation of deep green margins that are nearly one and a half to twice as wide as its sport parent 'Rainforest Sunrise'. The flower scapes of 'Pocketful of Sunshine' are taller than either 'Little Aurora' or 'Little Sunspot'.

There are over 4,500 cultivars registered with The American *Hosta* Society, which is the International Cultivar Registration Authority for the genus *Hosta*. *Hosta* 'Pocketful of Sunshine' differs from these and all unregistered cultivars known to the inventor in the following combined traits:

1. Compact dense habit and rapid growth rate
2. Leaves with yellow centers and broad deep green margins
3. Thick substance leaves with distinct cupping habit.
4. Light lavender flowers.
5. Leaves becoming rugose with maturity.

BRIEF DESCRIPTION OF THE DRAWINGS

The photographs of the new plant demonstrate the overall appearance of the newly propagated plant at about 2 months old, including the unique traits, grown in a partially shaded greenhouse with supplemental HID lighting, during the shorter day length part of the year, in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
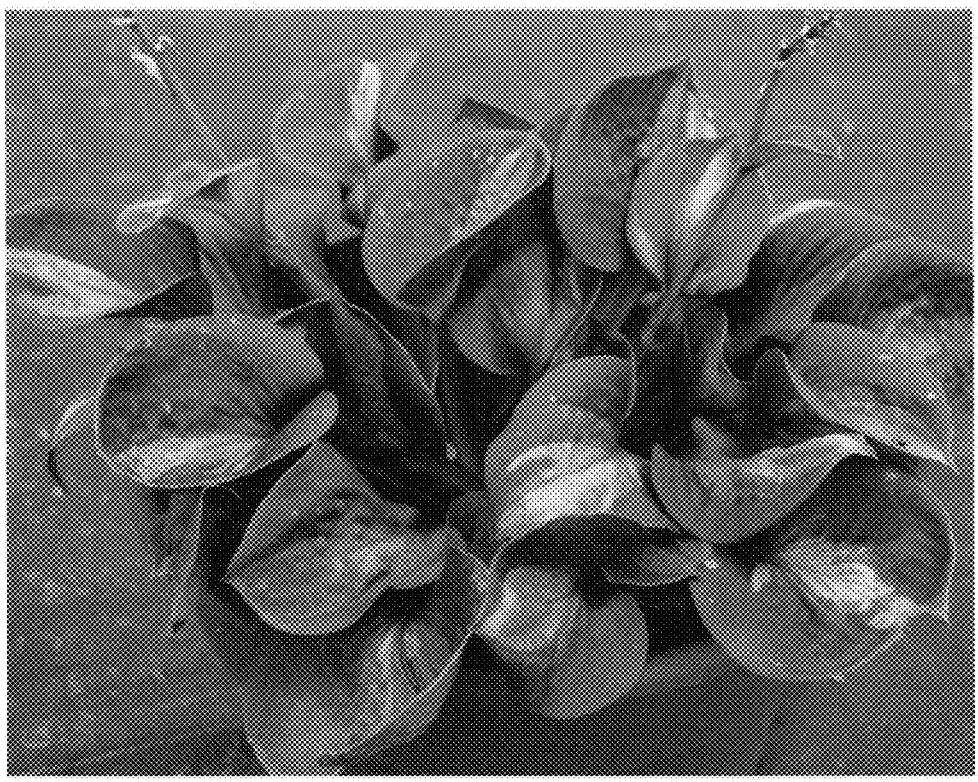
FIG. 1 shows a two-year old plant of *Hosta* 'Pocketful of Sunshine' grown in a greenhouse under 50% shade.
Figure 2:
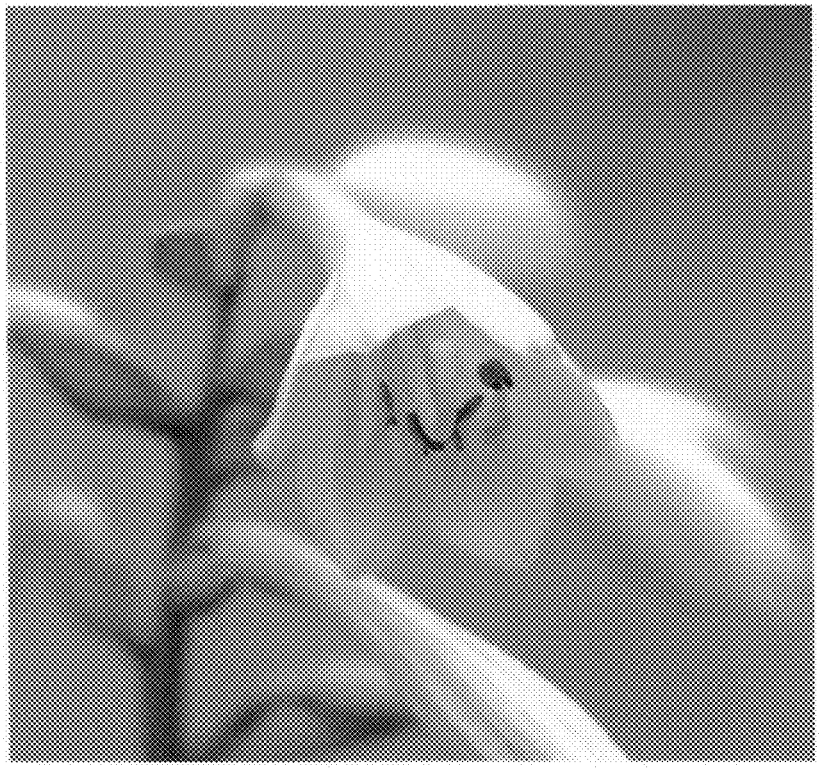
FIG. 2 shows a close-up of the flower of *Hosta* 'Pocketful of Sunshine'.

The following descriptions and color references are based on the 2001 edition of The Royal Horticultural Society Colour Chart except where common dictionary terms are used. The new plant, *Hosta* 'Pocketful of Sunshine', has not been observed under all possible environments. The phenotype may vary slightly with different environmental conditions, such as temperature, light, fertility, moisture and specimen maturity, but without any change in the genotype. The following observations and size descriptions are of a two-year old plant in a greenhouse in Zeeland, Mich. under 50% shade with supplemental water and light fertilizer.

Botanical classification: *Hosta* hybrid.

Parentage: Uninduced whole plant mutation of *Hosta* 'Rainforest Sunrise' (not patented).

Propagation method: By sterile laboratory tissue culture division and garden division.

Growth rate: Rapid.

Crop time: Summer growing 10 to 12 weeks to finish in a one-liter container. Time to initiate roots from tissue culture about two weeks.

Plant description:

*Plant shape and habit*.—Hardy, herbaceous, mounded, forming perennial with basal rosette of leaves, usually bilateral and radially symmetrical, spreading by rhizomes.

*Roots*.—Normal, fleshy, lightly branching, cream-colored in normal soil.

*Plant size*.—Foliage height about 20.0 cm tall; width of plant is approximately 48.0 cm at the widest point.

Foliage description:

*Leaf blade*.—Cordate to rounded-apiculate leaf base with rounded-apiculate apex, typically bilaterally symmetrical, entire margins, mostly flat blades with impressed veins; top surface and bottom surface lustrous, becoming rugose with maturity, cupped with leaf center concaved.

*Leaf blade size*.—About 11.0 cm wide and 11.5 cm long; margin width variable average about 3.0 cm wide on each side.

*Stomata*.—In comparison to parent, *Hosta* 'Rainforest Sunrise', the new plant's stomata are about 40% larger; chromosome counts by microscopy and DNA weight measurements by flow cytometry have not been preformed.

*Blade color*.—After flowering adaxial (top) margin dark green between RHS 137A and RHS 139A, adaxial center yellow more yellow than RHS 151A and RHS 151D and more green than RHS 160A, abaxial (underside) margin nearest RHS 137C and center nearest RHS 146C; at flowering time or earlier adaxial margin nearest RHS 137A, adaxial center nearest RHS N144A, abaxial margin more green than RHS 144A and more yellow than RHS 137A, abaxial center nearest RHS N144A.

*Veins*.—Parallel veins, nearly the same color as surrounding top and bottom leaf surfaces.

*Petioles*.—10 to 12 cm long, about 1.5 to 2.0 cm wide.

*Petiole color*.—Showing variegation similar to leaf blade with dark green margins and lighter center; margins adaxial and abaxial nearest RHS 137A and centers adaxial and abaxial between RHS N144A and RHS N144C.

Flower description:

*Buds*.—One day before opening — clavate with bluntly acute apex and longer thin base; light lavender in color, lighter than RHS 76D; about 4.2 cm long and 1.2 cm diameter at widest part.

*Flowers*.—Funnelform; about 2.8 cm wide and 5.0 cm long, (distal flowers opening smaller); remain open for a normal period, usually one to two days on or cut from plant; scapes remain effective from end June into mid July in Zeeland, Mich.; each scape having about 16 flowers; no detectable fragrance.

*Tepal*.—Two identical sets of three fused at the basal two thirds; acute apex; margins entire; about 4.0 cm long and 8 mm wide.

*Tepal color*.—Light lavender, outer surface very light, near white, much lighter than RHS 76D; inner surface center between RHS 76C and RHS 69C, inner margin nearly white, lighter than RHS N155D; both inner and outer tepal tip is green, nearest RHS 144A.

*Peduncle*.—Cylindrical, glaucous; about 32.0 cm long and 5.0 mm diameter at base.

*Peduncle color*.—Nearest RHS 147C.

*Pedicel*.—Cylindrical, glaucous; about 1.0 cm long and 2.0 mm diameter; slightly curved downward.

*Pedicel color*.—Lighter than RHS 148D.

*Bract*.—Each flower subtended by a bract; acute apex, base attached directly to scape; about 2.5 cm long and 8.0 mm wide, bracts decrease in size distally.

*Bract color*.—Margins of inner and outer surface nearest RHS 148C; center of inner and outer surface nearest RHS 147D; drying four days to one week post anthesis.

*Gynoecium*.—Single. Style: about 4.8 cm long, 1.0 mm diameter, curled upward at distal 1.2 cm; style color lighter than RHS 155D. Stigma: 1 mm to 2 mm in diameter, lighter than RHS 155D. Ovary: superior, oblong, about 7.0 mm long and 3.0 mm diameter, color nearest RHS 145A.

*Androecium*.—Filaments: six, about 1.0 mm in diameter and 4.0 cm long, curving upward the last 0.7 cm; filament color lighter than RHS 155D. Anther: dorsifixed, oblong elliptic, about 2.0 mm long and 1.0 mm diameter; color nearest RHS N187B. Pollen: round, less than 0.1 mm diameter; color nearest RHS 17A.

Fruit and seeds: Have not yet been observed.

Disease and pest resistance: Slug feeding on mature plants has not been noticed. Other disease or pest resistance beyond that common to *hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *hostas*.

I claim:

1. A new and distinct ornamental *Hosta* plant named 'Pocketful of Sunshine' as herein described and illustrated, with rounded, thick, coriaceous leaves with very wide dark green margins and yellow centers, light lavender flowers, suitable as a potted plant, for the garden, and for cut flower or leaf arrangements.

* * * * *